United States Patent
Utsumi et al.

(10) Patent No.: US 11,796,503 B2
(45) Date of Patent: Oct. 24, 2023

(54) WATER DETECTING DEVICE AND METHOD OF WATER DETECTION

(71) Applicant: HONDA MOTOR CO., LTD., Tokyo (JP)

(72) Inventors: Hidetoshi Utsumi, Tochigi-ken (JP); Takehiro Fukushima, Tochigi-ken (JP); Shunsuke Konishi, Tochigi-ken (JP); Yuichi Hori, Tochigi-ken (JP); Hodaka Tsuge, Tochigi-ken (JP)

(73) Assignee: HONDA MOTOR CO., LTD., Tokyo (JP)

( * ) Notice: Subject to any disclaimer, the term of this patent is extended or adjusted under 35 U.S.C. 154(b) by 229 days.

(21) Appl. No.: 17/200,956

(22) Filed: Mar. 15, 2021

(65) Prior Publication Data

US 2021/0293751 A1  Sep. 23, 2021

(30) Foreign Application Priority Data

Mar. 17, 2020 (JP) ................................. 2020-046060

(51) Int. Cl.
| | |
|---|---|
| H01M 8/04 | (2016.01) |
| G01N 27/48 | (2006.01) |
| G01N 33/18 | (2006.01) |
| H01M 8/04492 | (2016.01) |
| H01M 8/10 | (2016.01) |

(52) U.S. Cl.
CPC ............. G01N 27/48 (2013.01); G01N 33/18 (2013.01); H01M 8/045 (2013.01); *H01M 2008/1095* (2013.01)

(58) Field of Classification Search
CPC .................................................... H01M 8/045
See application file for complete search history.

(56) References Cited

U.S. PATENT DOCUMENTS

| | | | |
|---|---|---|---|
| 2001/0005557 A1 | 6/2001 | Yosida et al. | |
| 2004/0195097 A1 | 10/2004 | Suzuki et al. | |
| 2013/0062215 A1* | 3/2013 | Kurashina | ................ C25B 9/73 |
| | | | 204/229.8 |
| 2018/0149631 A1 | 5/2018 | Aoki et al. | |
| 2020/0036020 A1 | 1/2020 | Haruki et al. | |

FOREIGN PATENT DOCUMENTS

| | | |
|---|---|---|
| CN | 102338769 | 2/2012 |
| CN | 110635155 | 12/2019 |
| JP | 2013-060625 | 4/2013 |
| JP | 2019-220414 | 12/2019 |

OTHER PUBLICATIONS

Chinese Office Action and Search Report for Chinese Patent Application No. 202110286482.1 dated Jul. 28, 2023.

* cited by examiner

*Primary Examiner* — Olatunji A Godo
(74) *Attorney, Agent, or Firm* — AMIN, TUROCY & WATSON, LLP (57) ABSTRACT

A voltage applying unit of a water detecting device applies, to a pair of electrodes, a voltage changing within an application range that includes a first voltage which is smaller than an electrolysis voltage of water and a second voltage which is larger than the electrolysis voltage of the water. A judging unit judges presence or absence of the water based on change in electric current measured by a current measuring unit when the voltage changing within the application range is applied to the pair of electrodes.

4 Claims, 10 Drawing Sheets

WATER DETECTING DEVICE AND METHOD OF WATER DETECTION

CROSS-REFERENCE TO RELATED APPLICATION

This application is based upon and claims the benefit of priority from Japanese Patent Application No. 2020-046060 filed on Mar. 17, 2020, the contents of which are incorporated herein by reference.

BACKGROUND OF THE INVENTION

Field of the Invention

The present invention relates to a water detecting device and a method of water detection for detecting water within a reactant gas flow field of a power generation cell.

Description of the Related Art

Generally, a solid polymer electrolyte fuel cell includes a membrane electrode assembly (MEA) configured by a solid polymer electrolyte membrane being sandwiched by an anode and a cathode. By the membrane electrode assembly being further sandwiched by separators (bipolar plates), there is configured a power generation cell (a unit fuel cell). By a certain number of the power generation cells being stacked, the power generation cells are used as a vehicle-mounted fuel cell stack, for example.

Between the cathode and the separator of the power generation cell, an oxygen-containing gas flow field that passes an oxygen-containing gas along the cathode is formed as a reactant gas flow field. Between the anode and the separator of the power generation cell, a fuel gas flow field that passes a fuel gas along the anode is formed as a reactant gas flow field. The oxygen-containing gas and the fuel gas (reactant gases) that have been supplied via these reactant gas flow fields are consumed by an electrochemical reaction (a power generating reaction) in the membrane electrode assembly, whereby power generation is performed.

In this kind of power generation cell, sometimes, there accumulates, in the reactant gas flow field, liquid water such as generation water generated due to the power generating reaction or condensation water occurring by condensation of water vapor in the reactant gas. There is concern that, if liquid water is present within the reactant gas flow field, flow of the reactant gas within the reactant gas flow field will be hindered, and power generation stability of the power generation cell will lower.

Accordingly, there has been proposed a water detecting device for detecting presence or absence of liquid water within a reactant gas flow field, as indicated in Japanese Laid-Open Patent Publication No. 2019-220414, for example. By presence or absence of liquid water within the reactant gas flow field being detected by the water detecting device, it becomes possible for there to be devised some kind of device for discharging the liquid water with a certain timing as required.

SUMMARY OF THE INVENTION

The present invention, which has been made in relation to this kind of technology, has an object of providing a water detecting device and a method of water detection that enable detection accuracy of liquid water within a reactant gas flow field to be improved.

One aspect of the present invention is a water detecting device provided in a power generation cell, the power generation cell having a reactant gas flow field through which a reactant gas flows along a membrane electrode assembly, the water detecting device including: a pair of electrodes provided at a position facing the reactant gas flow field, the electrodes being spaced from each other; a voltage applying unit configured to apply a voltage to the pair of electrodes; a current measuring unit configured to measure an electric current flowing between the pair of electrodes; and a judging unit configured to judge presence or absence of liquid water within the reactant gas flow field based on a measurement result of the current measuring unit, the voltage applying unit being configured to change the voltage applied to the pair of electrodes within an application range that includes a first voltage which is smaller than an electrolysis voltage of the water and a second voltage which is larger than the electrolysis voltage of the water, and the judging unit being configured to judge presence or absence of the water based on change in the electric current measured by the current measuring unit when the voltage applied to the pair of electrodes is changed within the application range.

Another aspect of the present invention is a method of water detection for detecting presence or absence of liquid water within a reactant gas flow field through which a reactant gas flows along a membrane electrode assembly of a power generation cell, the method including: a judgment voltage applying step of applying a voltage to a pair of electrodes provided at a position facing the reactant gas flow field, the electrodes being spaced from each other, the voltage changing within an application range that includes a first voltage and a second voltage, the first voltage being smaller than an electrolysis voltage of the water, the second voltage being larger than the electrolysis voltage of the water; and a judging step of judging presence or absence of water within the reactant gas flow field, based on change in electric current flowing between the pair of electrodes measured by a current measuring unit when the voltage changing within the application range is applied to the pair of electrodes.

In the case of an electric current not being detected between the pair of electrodes to which a voltage is applied, the electrodes are in an electrically isolated state, and thus it can be judged that liquid water is not present between the electrodes. On the other hand, in the case of an electric current having been detected between the electrodes to which the voltage is applied, one of the reasons for the current being detected may be that the electric current is flowing via liquid water present between the electrodes. However, as another reason for the current being detected, there may be a case in which short-circuiting occurs due to, for example, electrical contact of the electrodes and constituent elements of the power generation cell. In other words, there may be a case in which an electric current flows between the electrodes even when liquid water is not present between the electrodes. There is therefore clearly concern that presence or absence of liquid water between the electrodes cannot be highly accurately detected by simply detecting an electric current between the electrodes alone.

In the present invention, a voltage changing within an application range that includes a first voltage which is smaller than an electrolysis voltage of the water and a second voltage which is larger than the electrolysis voltage of the water is applied to the pair of electrodes. Moreover, presence or absence of liquid water is judged based on change in an electric current measured by a current measuring unit when the voltage changing within the application range is applied to the pair of electrodes. In the case of liquid water being present between the electrodes, a way of changing of the electric current differs between before the voltage applied to the pair of electrodes exceeds the electrolysis voltage of the water and after the voltage applied to the pair of electrodes has exceeded the electrolysis voltage of the water. On the other hand, in the case of short-circuiting occurring between the electrodes, there is no particular change in the way of changing of the electric current between before the voltage applied to the pair of electrodes exceeds the electrolysis voltage of the water and after the voltage applied to the pair of electrodes has exceeded the electrolysis voltage of the water.

It is therefore possible to avoid, based on the above-described change in the electric current, a situation that short-circuiting of the electrodes, or the like, is mistakenly detected as liquid water being present between the electrodes. As a result, it becomes possible for detection accuracy of liquid water within the reactant gas flow field to be improved.

The above and other objects, features, and advantages of the present invention will become more apparent from the following description when taken in conjunction with the accompanying drawings, in which a preferred embodiment of the present invention is shown by way of illustrative example.

DESCRIPTION OF THE PREFERRED EMBODIMENTS

A preferred embodiment of a water detecting device and a method of water detection according to the present invention will be presented and described in detail with reference to the accompanying drawings. Note that, in the following drawings, configuring elements displaying the same or similar functions and advantages will sometimes be assigned with the same reference symbols, and that repeated descriptions of those configuring elements will sometimes be omitted.

Figure 1:
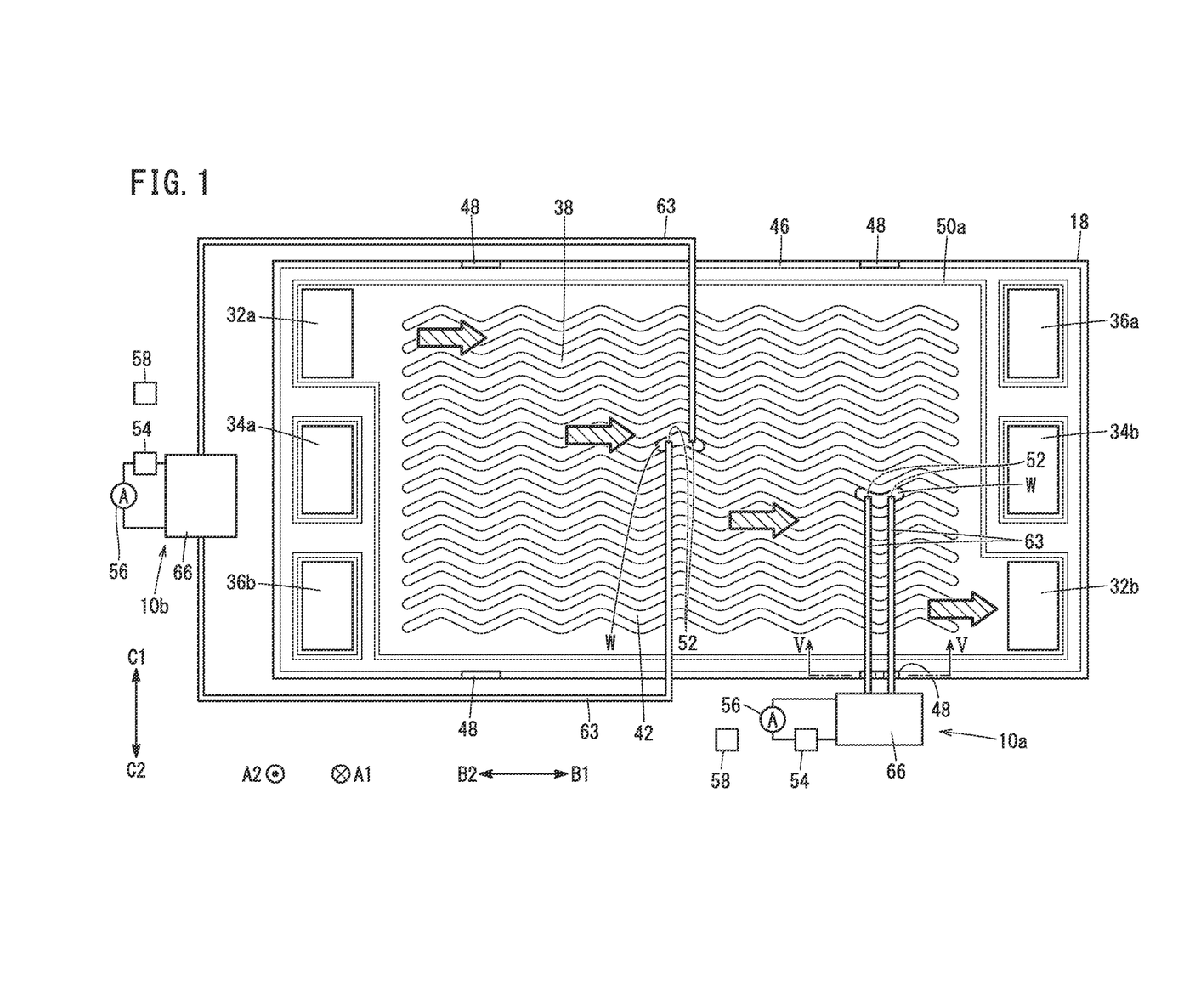
FIG. 1 is a diagram viewing from an oxygen-containing gas flow field side a second separator that has disposed therein a water detecting device according to an embodiment of the present invention.
Figure 2:
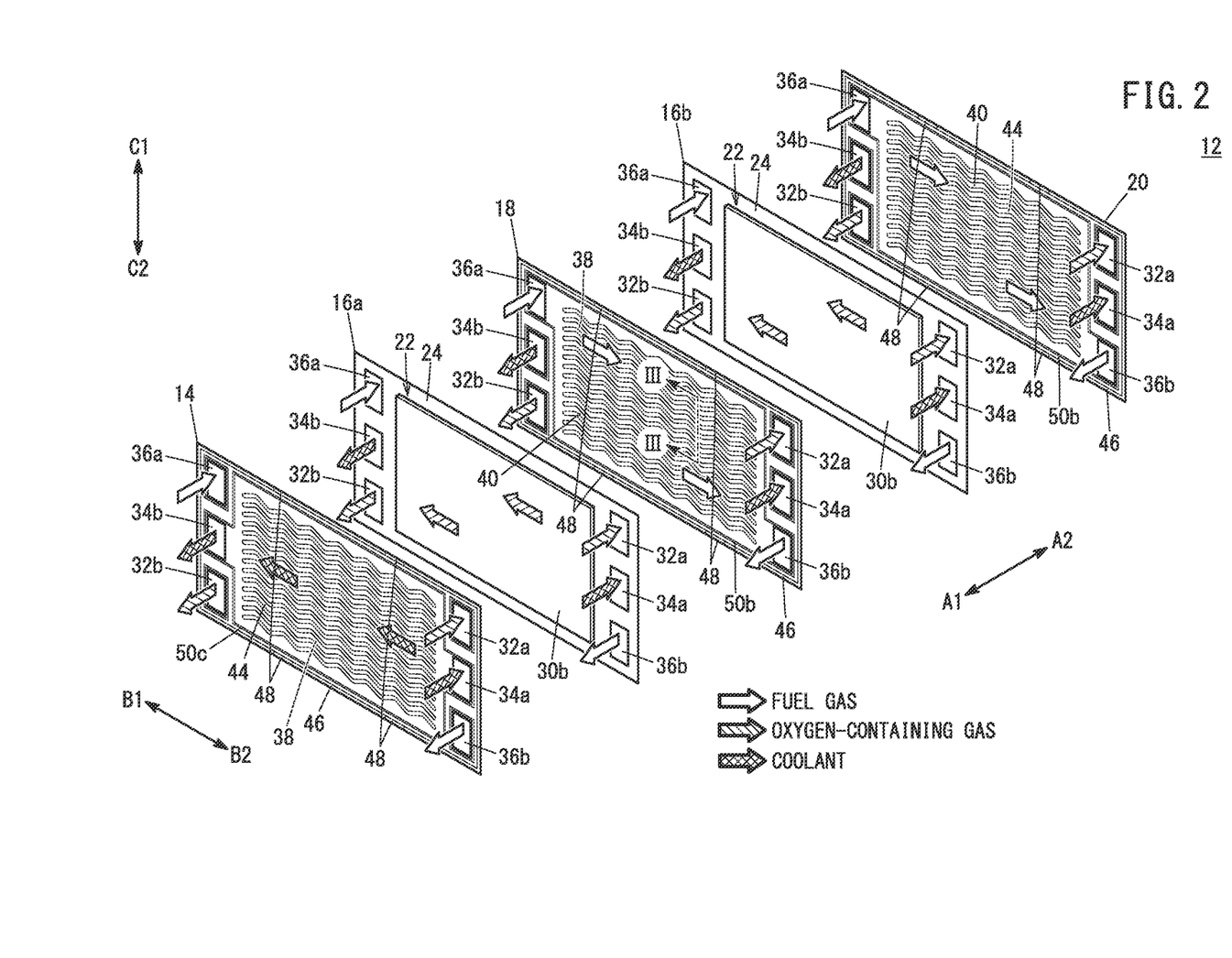
FIG. 2 is an exploded perspective view of a power generation cell including a first separator of FIG. 1.

As an example of a power generation cell provided with water detecting devices 10a, 10b according to the present embodiment shown in FIG. 1, there may be cited a power generation cell 12 shown in FIG. 2. Accordingly, first, configuration of the power generation cell 12 will be simply described mainly with reference to FIGS. 1 to 3. Note that a power generation cell capable of being provided with the water detecting devices 10a, 10b is not limited to the power generation cell 12 of FIG. 2, and that the water detecting devices 10a, 10b can be similarly applied to a variety of power generation cells in which liquid water may accumulate within a reactant gas flow field as will be mentioned later.

By, for example, a plurality of the power generation cells 12 being stacked in an arrows A1, A2 direction (a horizontal direction) of FIG. 2 or an arrows C1, C2 direction (a gravity direction) of FIG. 2, and being applied with a tightening load (a compressive load) in a stacking direction, the power generation cells 12 are capable of configuring an unillustrated fuel cell stack. The fuel cell stack is capable of, for example, being employed installed in an unillustrated fuel cell electric vehicle or being employed as a stationary type, and so on.

As shown in FIG. 2, the power generation cell 12 is configured by there being stacked therein in the following order a first separator 14, a resin frame equipped MEA 16a, a second separator 18, a resin frame equipped MEA 16b, and a third separator 20. The first separator 14, the second separator 18, and the third separator 20 are each a metal separator configured from the likes of a steel plate, a stainless steel plate, an aluminum plate, or a plating-treated steel plate, for example. Hereafter, in such cases as when the first separator 14, the second separator 18, and the third separator 20 are not specifically distinguished, they will also be collectively referred to simply as "separators". The separator has a rectangular shape when viewed in the arrows A1, A2 direction, and, due to press processing, or the like, has its cross section formed in an uneven shape. Note that the separator may be a carbon separator.

Figure 3:
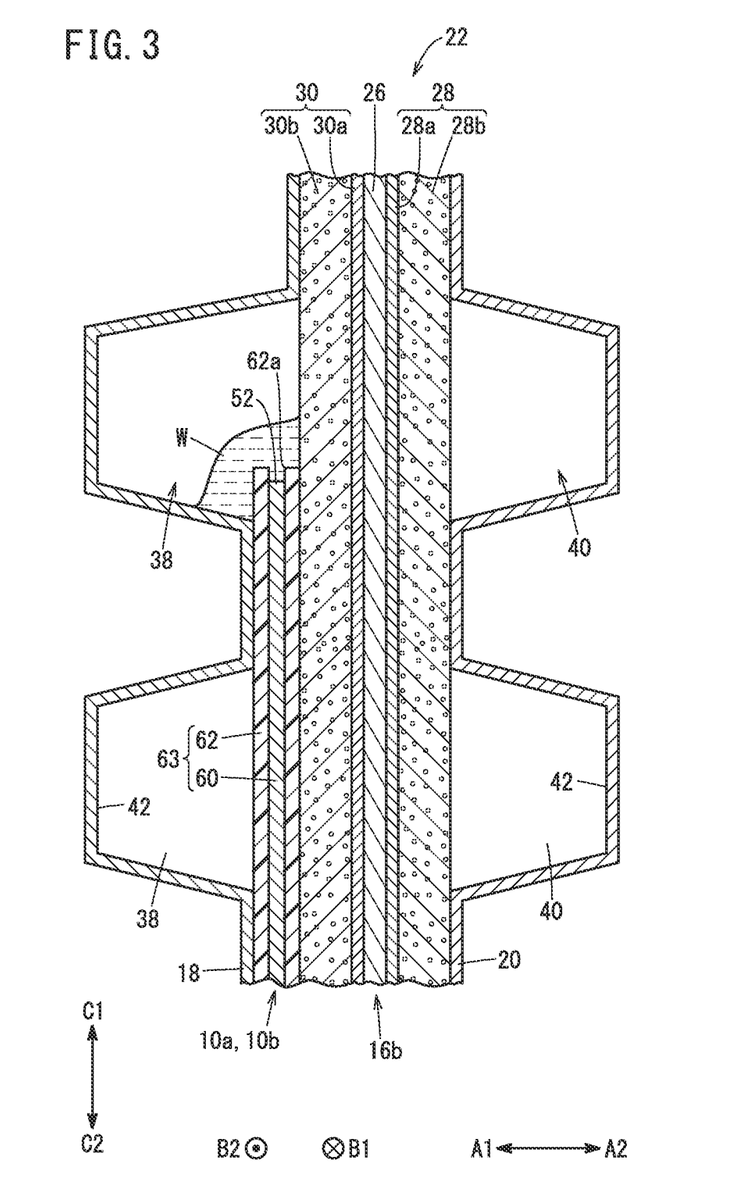
FIG. 3 is a cross-sectional view taken along the line III-III of the power generation cell of FIG. 2 looking in a direction of the arrows, that includes a cross section of the water detecting device of FIG. 1.

The resin frame equipped MEAs 16a, 16b are each configured by a resin frame member 24 being joined to an outer periphery of a membrane electrode assembly (MEA) 22. As shown in FIG. 3, the membrane electrode assembly 22 has: an electrolyte membrane 26; and an anode 28 and cathode 30 that sandwich the electrolyte membrane 26. As the electrolyte membrane 26, there may be used a solid polymer electrolyte membrane (a cation-exchange membrane) such as a water-including perfluorosulfonic acid membrane, or there may be used an HC (hydrocarbon)-based electrolyte membrane, for example.

The cathode 30 has: a cathode catalyst layer 30a which is joined to a surface on an arrow A1 side of the electrolyte membrane 26; and a cathode gas diffusion layer 30b which is stacked on the cathode catalyst layer 30a. The anode 28 has: an anode catalyst layer 28a which is joined to a surface on an arrow A2 side of the electrolyte membrane 26; and an anode gas diffusion layer 28b which is stacked on the anode catalyst layer 28a.

The cathode catalyst layer 30a is formed by, for example, porous carbon particles having a platinum alloy supported on their surfaces being uniformly coated on a surface of the cathode gas diffusion layer 30b along with an ionic conductive polymer binder. The anode catalyst layer 28a is formed by, for example, porous carbon particles having a platinum alloy supported on their surfaces being uniformly coated on a surface of the anode gas diffusion layer 28b along with an ionic conductive polymer binder.

The cathode gas diffusion layer 30b and the anode gas diffusion layer 28b are formed from a conductive porous sheet such as carbon paper or carbon cloth. The resin frame member 24 of FIG. 2, which is configured from a frame-shaped film, has its inner peripheral end edge portion sandwiched between an outer peripheral end edge portion of the cathode gas diffusion layer 30b of FIG. 3 and an outer peripheral end edge portion of the anode gas diffusion layer 28b of FIG. 3, for example. Note that the electrolyte membrane 26 may be projected outwardly, without the resin frame member 24 being employed. Moreover, a frame-shaped film may be provided on both sides of the outwardly projecting electrolyte membrane 26.

As shown in FIG. 2, in one end edge portion in a longitudinal direction (an end portion on an arrow B2 side) of the rectangular power generation cell 12, an oxygen-containing gas inlet passage 32a, a coolant inlet passage 34a, and a fuel gas outlet passage 36b are arranged in a vertical direction (the arrows C direction), each passage extending through the power generation cells 12 in a stacking direction (the arrows A1, A2 direction). The oxygen-containing gas inlet passage 32a is supplied with an oxygen-containing gas, for example, as an oxygen-containing gas. The coolant inlet passage 34a is supplied with at least any one of the likes of pure water, ethylene glycol, and oil, for example, as a coolant. The fuel gas outlet passage 36b has discharged therefrom a hydrogen-containing gas, for example, as a fuel gas. Note that hereafter, the oxygen-containing gas and the fuel gas will also be collectively referred to as "reactant gases".

In the other end edge portion in the longitudinal direction (an end portion on an arrow B1 side) of the power generation cell 12, a fuel gas inlet passage 36a supplied with the fuel gas, a coolant outlet passage 34b discharging the coolant, and an oxygen-containing gas outlet passage 32b discharging the oxygen-containing gas are arranged in the vertical direction (the arrows C direction), each passage extending through the power generation cells 12 in the stacking direction.

Hereafter, the oxygen-containing gas inlet passage 32a, the coolant inlet passage 34a, the fuel gas outlet passage 36b, the fuel gas inlet passage 36a, the coolant outlet passage 34b, and the oxygen-containing gas outlet passage 32b will also be collectively referred to simply as "passages".

In-between the first separator 14 of FIG. 2 and the cathode gas diffusion layer 30b of the resin frame equipped MEA 16a, there is provided an oxygen-containing gas flow field 38 that communicates with the oxygen-containing gas inlet passage 32a and the oxygen-containing gas outlet passage 32b of FIG. 1.

In-between the second separator 18 of FIG. 2 and the anode gas diffusion layer 28b of the resin frame equipped MEA 16a, there is provided a fuel gas flow field 40 that communicates with the fuel gas inlet passage 36a and the fuel gas outlet passage 36b. In-between the second separator 18 of FIG. 2 and the cathode gas diffusion layer 30b of the resin frame equipped MEA 16b, there is provided an oxygen-containing gas flow field 38 that communicates with the oxygen-containing gas inlet passage 32a and the oxygen-containing gas outlet passage 32b of FIG. 1.

In-between the third separator 20 of FIG. 2 and the anode gas diffusion layer 28b of the resin frame equipped MEA 16b, there is provided a fuel gas flow field 40 that communicates with the fuel gas inlet passage 36a and the fuel gas outlet passage 36b.

Hereafter, the oxygen-containing gas flow field 38 and the fuel gas flow field 40 will also be collectively referred to as "reactant gas flow fields". Each of the separators has formed therein a plurality of wavy flow grooves 42 (or linear flow grooves) that are arranged in the arrows C1, C2 direction, and these wavy flow grooves 42 form the reactant gas flow fields. Each of the wavy flow grooves 42 meanders in a wave-shaped manner in the arrows B1, B2 direction.

In power generation cells 12 that are adjacent to each other, a surface on an arrow A1 side of the first separator 14 configuring one of the power generation cells 12 and a surface on an arrow A2 side of the third separator 20 configuring the other of the power generation cells 12, face each other. In-between these first separator 14 and third separator 20, there is provided a coolant flow field 44 that communicates with the coolant inlet passage 34a and the coolant outlet passage 34b.

Both surfaces of each of the separators each have a seal member 46 provided along their outer peripheral edge portion. The seal member 46 seals an inside and an outside in a surface direction of the separator surrounded by the seal member 46. As shown in FIGS. 1 and 2, on each of both end sides in a short side direction (the arrows C1, C2 direction) and both sides in a long side direction (the arrows B1, B2 direction) further to a center side than each of the passages in the outer peripheral edge portion of each of the separators, there is provided a flopper 48. The flopper 48 has its projection height from the separator set higher than a projection height from the separator of the seal member 46. Such a flopper 48 can be employed in the likes of positioning when stacking the separators and resin frame equipped MEAs 16a, 16b, for example.

As shown in FIGS. 1 and 2, a surface on the arrow A2 side of the first separator 14 and a surface on the arrow A2 side of the second separator 18 are each provided with a seal member 50a that integrally surrounds the oxygen-containing gas inlet passage 32a, the oxygen-containing gas outlet passage 32b, and the oxygen-containing gas flow field 38 to seal an inside thereof from an outside thereof in the surface direction.

As shown in FIG. 2, a surface on the arrow A1 side of the second separator 18 and a surface on the arrow A1 side of the third separator 20 are each provided with a seal member 50b that integrally surrounds the fuel gas inlet passage 36a, the fuel gas outlet passage 36b, and the fuel gas flow field 40 to seal an inside thereof from an outside thereof in the surface direction.

A surface on the arrow A1 side of the first separator 14 of FIG. 2 and an unillustrated surface on the arrow A2 side of the third separator 20 are each provided with a seal member 50c that integrally surrounds the coolant inlet passage 34a, the coolant outlet passage 34b, and the coolant flow field 44 to seal an inside thereof from an outside thereof in the surface direction. The seal members 46, 50a, 50b, and 50c are each formed from an elastomer such as rubber or resin having elasticity, for example.

In the case of performing a power generating operation by a fuel cell stack having stacked therein a plurality of the power generation cells 12 configured as described above, the fuel gas inlet passage 36a of FIG. 2 is supplied with the fuel gas, the oxygen-containing gas inlet passage 32a is supplied with the oxygen-containing gas, and the coolant inlet passage 34a is supplied with the coolant. The fuel gas that has been supplied to the fuel gas inlet passage 36a is introduced to the fuel gas flow field 40 and flows along the anode 28. The oxygen-containing gas that has been supplied to the oxygen-containing gas inlet passage 32a is introduced to the oxygen-containing gas flow field 38 and flows along the cathode 30.

In the membrane electrode assembly 22, the fuel gas supplied to the anode 28 and the oxygen-containing gas supplied to the cathode 30 are consumed by an electrochemical reaction (a power generating reaction) in the anode catalyst layer 28a and the cathode catalyst layer 30a, and power generation is performed. Residual fuel gas that has not been consumed in the power generating reaction is discharged from the fuel gas outlet passage 36b, and residual oxygen-containing gas that has not been consumed in the power generating reaction is discharged from the oxygen-containing gas outlet passage 32b. On the other hand, the coolant that has been supplied to the coolant inlet passage 34a flows along the coolant flow field 44 to cool the membrane electrode assembly 22, and is then discharged from the coolant outlet passage 34b.

In the above-described power generating reaction, protons generated by ionization of hydrogen gas in the fuel gas, electrons subsequent to energization by an external load, and oxygen gas in the oxygen-containing gas combine so that liquid water (generation water) occurs.

Moreover, in order for the electrolyte membrane 26 to be made to express good proton conductivity, the reactant gas generally contains water vapor due to it being required that the electrolyte membrane 26 is maintained in a wet state, and so on. Condensation of this water vapor also results in liquid water (condensation water) occurring. Liquid water of the likes of these generation water and condensation water sometimes accumulates within the reactant gas flow field.

The water detecting devices 10a, 10b according to the present embodiment of FIG. 1 are provided in the power generation cell 12 in order to detect presence or absence of liquid water W within the reactant gas flow field. Note that hereafter, "water W" will be assumed to be liquid water, unless otherwise specifically described. The water detecting devices 10a, 10b will be described with additional reference to FIGS. 4 to 6.

These water detecting devices 10a, 10b detect presence or absence of water W within the oxygen-containing gas flow field 38 between the second separator 18 and the cathode gas diffusion layer 30b of the resin frame equipped MEA 16b. However, the water detecting devices 10a, 10b can also similarly detect presence or absence of water W within the oxygen-containing gas flow field 38 between the first separator 14 and the cathode gas diffusion layer 30b of the resin frame equipped MEA 16a.

Moreover, the water detecting devices 10a, 10b can also similarly detect presence or absence of water W within each of the fuel gas flow field 40 between the second separator 18 and the anode gas diffusion layer 28b of the resin frame equipped MEA 16a, and the fuel gas flow field 40 between the third separator 20 and the anode gas diffusion layer 28b of the resin frame equipped MEA 16b.

FIG. 1 illustrates the two water detecting devices 10a, 10b provided within the oxygen-containing gas flow field 38 between the second separator 18 and the cathode gas diffusion layer 30b of FIG. 3. However, the number of water detecting devices 10a, 10b provided in the reactant gas flow field is not specifically limited. Moreover, there may be provided one or a plurality of the water detecting devices 10b alone, without the water detecting device 10a being provided, or there may be provided one or a plurality of the water detecting devices 10a alone, without the water detecting device 10b being provided.

Figure 4:
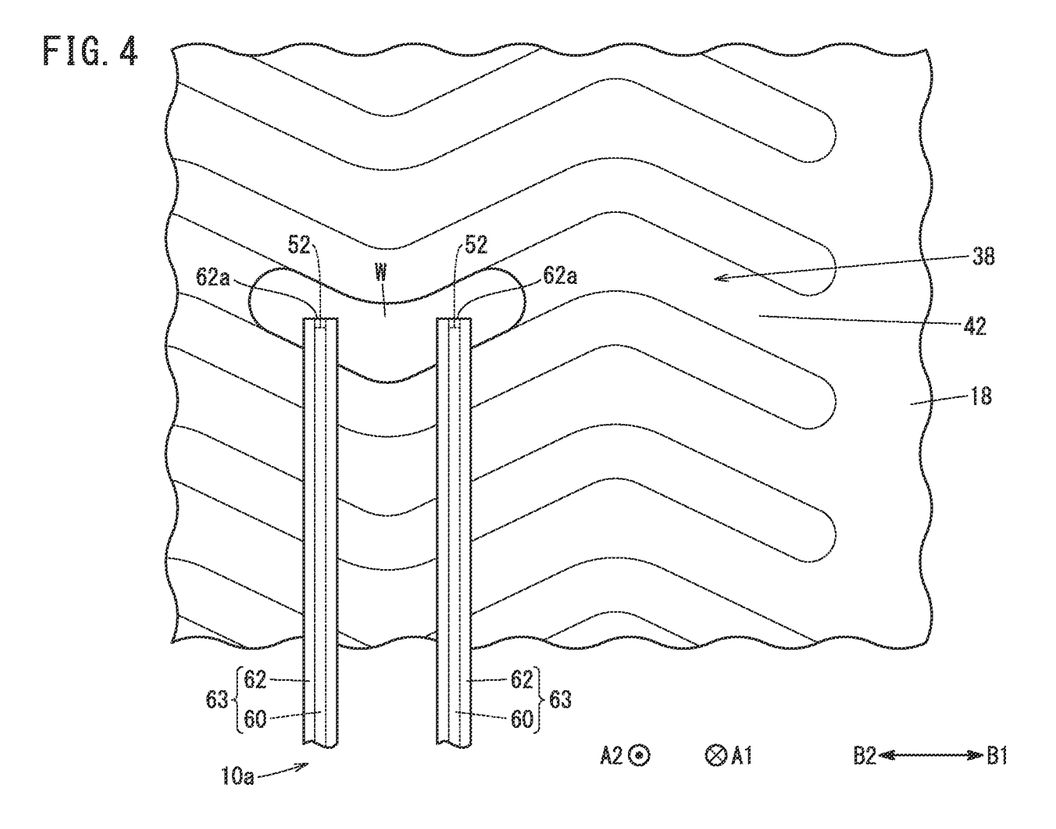
FIG. 4 is an enlarged view of principal portions of the water detecting device of FIG. 1.

The water detecting devices 10a, 10b each comprise a pair of electrodes 52, a voltage applying unit 54, a current measuring unit 56, and a judging unit 58. As shown in FIGS. 3 and 4, the pair of electrodes 52 are provided on tip portions of two conductive members 60. Each of the conductive members 60, which have a substantially circular columnar shape configured from the likes of a metal-made conducting wire, for example, has its outer periphery excluding its tip portion covered by a substantially cylindrical insulating film 62.

The insulating film 62 is made of an insulative material enabling a portion excluding the tip portion of the conductive member 60 to be electrically insulated from outside of the conductive member 60. A tip in an axial direction of the insulating film 62 is provided with an opening 62a. Therefore, the tip portion of the conductive member 60 is exposed to the outside of the insulating film 62 via the opening 62a of the insulating film 62. The electrode 52 is thus made up of the tip portion of the conductive member 60 exposed to the outside of the insulating film 62. Note that the conductive member 60 and the insulating film 62 may have a belt-shape (film-shape).

In the present embodiment, a length of the insulating film 62 in an axial direction (a length in an extension direction) on a tip side thereof is set so as to be slightly longer than a length of the conductive member 60 in an axial direction (a length in an extension direction) on a tip side thereof. Therefore, the tip portion of the conductive member 60 that forms the electrode 52 faces the outside of the insulating film 62 via the opening 62a at a position slightly retracted toward a base end side from the tip of the insulating film 62. This makes it possible for water W to intrude inside the insulating film 62 from the opening 62a at the tip of the insulating film 62, and for the electrode 52 and the water W to thereby contact each other, as shown in FIG. 3. In this case, since the electrode 52 is disposed inside the insulating film 62, it is possible to avoid a situation in which constituent elements (configurations other than water W) of the power generation cell 12 come into contact with the electrode 52, for example. As a result, it becomes possible for detection accuracy of water W by the electrode 52 to be improved.

As shown in FIGS. 1 and 4, the pair of electrodes 52 are provided at positions facing the oxygen-containing gas flow field 38 (the reactant gas flow field) and spaced from each other. In the case of the reactant gas flow field being formed by a plurality of the wavy flow grooves 42 as in the present embodiment, the pair of electrodes 52 are disposed within the same wavy flow groove 42 at a distance in an extension direction of the wavy flow groove 42.

Moreover, as shown in FIG. 1, the pair of electrodes 52 are preferably disposed in a downstream region where water generated in the oxygen-containing gas flow field 38 readily accumulates (i.e., on a side close to the oxygen-containing gas outlet passage 32b of the oxygen-containing gas flow field 38). However, disposition of the pair of electrodes 52 is not specifically limited in this way. The electrodes may be disposed in an upstream region of the oxygen-containing gas flow field 38 (on a side close to the oxygen-containing gas inlet passage 32a of the oxygen-containing gas flow field 38) or between the upstream region and the downstream region of the oxygen-containing gas flow field 38.

The conductive member 60 covered by the insulating film 62 (hereafter, also referred to as wiring portion 63) is arranged between the second separator 18 and the resin frame equipped MEA 16b of the power generation cell 12. In the water detecting device 10a according to the present embodiment, the two wiring portions 63 are inserted between the second separator 18 and the resin frame equipped MEA 16b from outside of the power generation cell 12 via one long side of the power generation cell 12.

Moreover, in the water detecting device 10b according to the present embodiment, one of the two wiring portions 63 is inserted between the second separator 18 and the resin frame equipped MEA 16b from outside of the power generation cell 12 via a long side on an arrow C1 side of the power generation cell 12. Moreover, the other of the two wiring portions 63 is inserted between the second separator 18 and the resin frame equipped MEA 16b from outside of the power generation cell 12 via another long side on an arrow C2 side of the power generation cell 12.

The water detecting device 10a and the water detecting device 10b are configured substantially similarly, except that insertion orientations of the wiring portions 63 with respect to the power generation cell 12 differ from each other as described above. Note that the two wiring portions 63 may be inserted between the second separator 18 and the resin frame equipped MEA 16b from any direction. Moreover, each of the wiring portions 63 may be immovably positioned by being adhered to at least one of the second separator 18 and the resin frame equipped MEA 16b, by an unillustrated adhesive agent.

As described above, in the fuel cell stack, a tightening load is applied in the stacking direction. Therefore, as shown in FIG. 3, the power generation cell 12 with the wiring portion 63 inserted between the second separator 18 and the resin frame equipped MEA 16b bends depending on thickness of the wiring portion 63. As a result, the second separator 18 and a portion of the resin frame equipped MEA 16b where the wiring portion 63 is not disposed are in contact with each other in the stacking direction.

As shown in FIG. 1, an end portion on an opposite side to an electrode 52 side of the wiring portion 63 protrudes out from the power generation cell 12. In other words, the wiring portion 63 is arranged traversing an outer peripheral edge portion of the power generation cell 12. Thus, in the case where the wiring portion 63 is disposed on the seal member 46 provided on an outer peripheral edge portion of the separator so as to intersect an extension direction of the seal member 46, an unillustrated adhesive agent is preferably provided between the wiring portion 63 and the seal member 46. As a result, it becomes possible for inside and outside of the outer peripheral edge portion of the power generation cell 12 to be maintained in a well-sealed state, even when the wiring portion 63 is inserted in the power generation cell 12.

Figure 5:
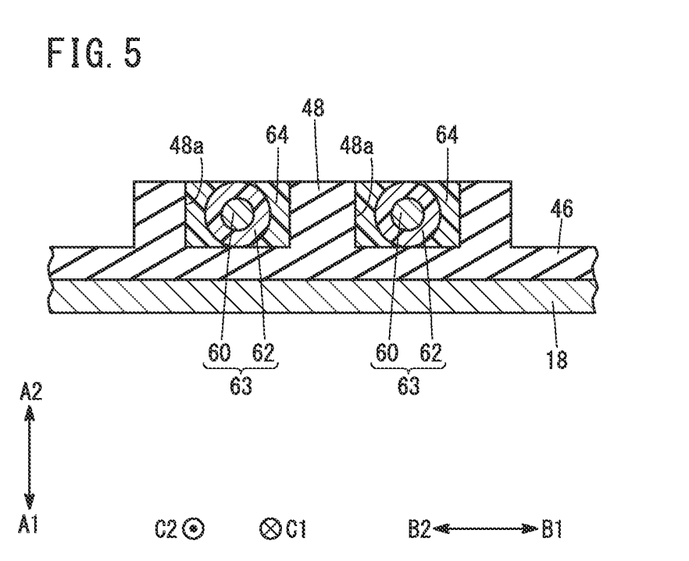
FIG. 5 is an enlarged cross-sectional view taken along the line V-V of FIG. 1 looking in a direction of the arrows.

Moreover, in the case of the wiring portion 63 traversing a portion provided with the flopper 48 of the separator, a cutout portion 48a is preferably formed in the flopper 48, as shown in FIG. 5. The cutout portion 48a is formed by part of the flopper 48 in its projecting direction being cut out in a direction in which the wiring portion 63 traverses. Part of the wiring portion 63 is housed inside the cutout portion 48a. In the present embodiment, two cutout portions 48a are formed in the flopper 48, correspondingly to the two wiring portions 63. The wiring portions 63 are housed respectively in these two cutout portions 48a. Moreover, a space between an inner wall of the cutout portion 48a and the wiring portion 63 is preferably filled with an adhesive agent 64. By provision of the cutout portion 48a and the adhesive agent 64 in this way too, it becomes possible for inside and outside of the outer peripheral edge portion of the power generation cell 12 to be maintained in a well-sealed state.

Note that short-circuiting sometimes occurs between the pair of electrodes 52. As an example of a reason therefor, there may be cited that an exposed portion exposed from the insulating film 62 occurs in the conductive member 60 in the wiring portion 63, and the exposed portion contacts the separator, the membrane electrode assembly 22, or the like.

As described above, the wiring portion 63 is inserted between the second separator 18 and the resin frame equipped MEA 16b. At this time, the wiring portion 63 abuts on the cathode gas diffusion layer 30b of the resin frame equipped MEA 16b. The cathode gas diffusion layer 30b is formed from a structure comprising fibers, such as carbon paper. Thus, there is concern that, due to fibers of the cathode gas diffusion layer 30b and the insulating film 62 of the wiring portion 63 making contact, the insulating film 62 will be damaged and peel from the conductive member 60 resulting in the exposed portion occurring.

Moreover, the electrolyte membrane 26 swells when its water content rises, and shrinks when its water content falls. When the electrolyte membrane 26 repeats swelling/shrinking due to the power generating operation of the fuel cell stack, it results in the wiring portion 63 inserted between the second separator 18 and the resin frame equipped MEA 16b also being subjected to repeated application of load. This also leads to concern that the insulating film 62 will peel from the conductive member 60 resulting in the exposed portion occurring.

As shown in FIG. 1, at the end portion of the wiring portion 63 disposed on the outside of the power generation cell 12, the voltage applying unit 54 and the current measuring unit 56 are electrically connected via a connecting terminal 66. The voltage applying unit 54 is configured from a power source or the like capable of applying a voltage to the pair of electrodes 52. Moreover, the voltage applying unit 54 is capable of applying to the pair of electrodes 52 a voltage that changes within an application range including a first voltage which is smaller than an electrolysis voltage of the water W and a second voltage which is larger than the electrolysis voltage of the water W.

The electrolysis voltage of the water W is a voltage at which electrolysis actually occurs in the water W that interposes and straddles between the pair of electrodes 52 within the reactant gas flow field, as shown in FIG. 4. This electrolysis voltage of the water W can be determined in advance by experiment, or the like, and, although not specifically limited, is capable of being set from a range of 1.23 to 1.5 V, for example. Note that 1.23 V is a theoretical value of the electrolysis voltage of the water W, and 1.5 V is a value taking into account effects of ions included in the water W and/or overvoltage. It is therefore preferable that, for example, the first voltage is a voltage smaller than 1.23 V, and the second voltage is a voltage larger than 1.5 V. In the present embodiment, the first voltage is set to 0.5 V, and the second voltage is set to 2.0 V, but the first and second voltages are not specifically limited to these values.

The voltage applying unit 54 may be configured to apply step voltages of 0 V, 0.1 V, 0.2 V, 0.3 V, 0.4 V, 0.5 V, 1.0 V, 1.5 V, 2.0 V, 3.0 V, 4.0 V, for example, as the voltage changing within the application range.

The voltage applying unit 54 may be configured to apply first selected voltages and second selected voltages to the pair of electrodes 52. The first selected voltages are a plurality of voltages selected from a first voltage range smaller than the electrolysis voltage of the water W. The first voltage is included in the first selected voltages. The second selected voltages are a plurality of voltages selected from a second voltage range larger than the electrolysis voltage of the water W. The second voltage is included in the second selected voltages.

For example, in the case where the electrolysis voltage of the water W is assumed to be 1.5 V and the above-described step voltages are applied by the voltage applying unit 54, the first selected voltages may be set as at least two voltages selected from 0.1 V, 0.2 V, 0.3 V, 0.4 V, 0.5 V, 1.0 V. Moreover, in this case, the second selected voltages may be set as at least two voltages selected from 2.0 V, 3.0 V, 4.0 V.

Furthermore, the voltage applying unit 54 may be configured to apply a detection voltage larger than the electrolysis voltage of the water W to the pair of electrodes 52. The detection voltage is preferably set to 2.0 V, for example. Note that voltage values of the detection voltage and the second voltage may be the same.

The current measuring unit 56 is configured from an ammeter or the like that, in the case where electric current flows between the pair of electrodes 52 applied with a voltage by the voltage applying unit 54, is capable of detecting a current between the electrodes 52 and measuring a current value.

The judging unit 58 is configured as an unillustrated computer comprising a CPU, a memory, and so on. Moreover, the judging unit 58 receives a signal from the current measuring unit 56, and judges presence or absence of water W within the reactant gas flow field based on a measurement result of the current measuring unit 56.

Figure 6:
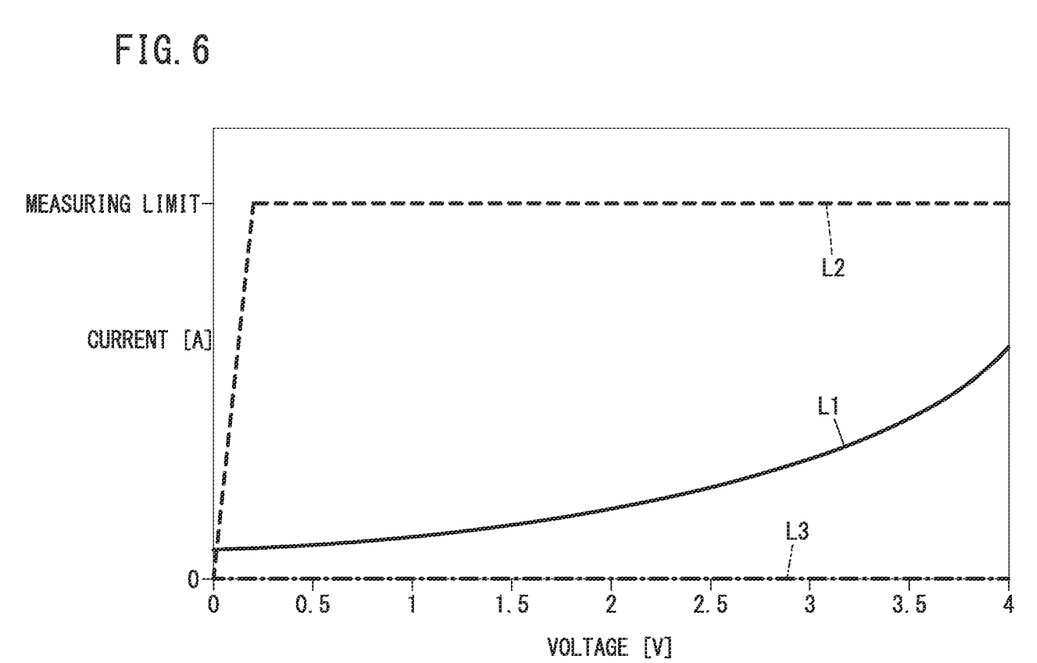
FIG. 6 is a graph showing a relationship of a voltage applied between electrodes and a current flowing between the electrodes in each of a case of water being present between the electrodes, a case of there being short-circuiting between the electrodes, and a case of there being no water present and no short-circuiting between the electrodes.

Now, in the case of water W being present between the pair of electrodes 52, there is an exponential relationship at least partially between the voltage applied to the pair of electrodes 52 (applied voltage) and the electric current flowing between the pair of electrodes 52 (inter-electrodes 52 current), as indicated by the solid line L1 in FIG. 6. In this case, a way of changing of the inter-electrodes 52 current differs between before the applied voltage exceeds the electrolysis voltage of the water W and after the applied voltage has exceeded the electrolysis voltage of the water W. In other words, a ratio at which the inter-electrodes 52 current increases due to the applied voltage being increased will be larger after the applied voltage has reached the electrolysis voltage of the water W than before the applied voltage reaches the electrolysis voltage of the water W.

On the other hand, in the case of short-circuiting occurring between the pair of electrodes 52, there is a proportional relationship in accordance with Ohm's law between the applied voltage and the inter-electrodes 52 current. At a time of this short-circuiting between the electrodes 52, the inter-electrodes 52 current increases in proportion to resistance between these electrodes 52 decreasing. In the present embodiment, when the pair of electrodes 52 have short-circuited, the inter-electrodes 52 current occurring when the first voltage and the second voltage are applied exceeds a measuring limit by the current measuring unit 56, as indicated by the broken line L2 in FIG. 6. In other words, the measuring limit of the current measuring unit 56 is set smaller than an electric current that flows between the pair of electrodes 52 when the first voltage and the second voltage are applied to the pair of electrodes 52 that are in short-circuit condition.

Hereafter, an electric current measured by the current measuring unit 56 when the first voltage is applied to the pair of electrodes 52 by the voltage applying unit 54 will also be called a first current. Moreover, an electric current measured by the current measuring unit 56 when the second voltage is applied to the pair of electrodes 52 by the voltage applying unit 54 will also be called a second current. In other words, when the pair of electrodes 52 have short-circuited, the first current and the second current reach the measuring limit of the current measuring unit 56.

Hence, in the case of short-circuiting occurring between the electrodes 52, an exponential relationship does not hold between the applied voltage and the inter-electrodes 52 current. In this case, there is no particular change in the way of changing of the inter-electrodes 52 current between before the applied voltage exceeds the electrolysis voltage of the water W and after the applied voltage has exceeded the electrolysis voltage of the water W. As a result, there is no particular change in the ratio at which the inter-electrodes 52 current increases due to the applied voltage being increased, between before the applied voltage reaches the electrolysis voltage of the water W and after the applied voltage has reached the electrolysis voltage of the water W.

Accordingly, the judging unit 58 judges presence or absence of the water W based on change in the electric current measured by the current measuring unit 56 when the voltage applied to the pair of electrodes 52 is changed within the application range. Specifically, the judging unit 58 judges water W not to be present between the pair of electrodes 52 within the reactant gas flow field and short-circuiting between the electrodes 52 not to be occurring either, in the case of an electric current between the electrodes 52 not being detected by the current measuring unit 56, as indicated by the one dot chain line L3 in FIG. 6.

As described above, in the case of the measuring limit of the current measuring unit 56 being set smaller than the inter-electrodes 52 current occurring during short-circuiting, the judging unit 58 may judge the water W to be present between the pair of electrodes 52 within the reactant gas flow field when the second current is larger than the first current. On the other hand, the judging unit 58 may judge short-circuiting to be occurring in the pair of electrodes 52 when both the first current and the second current have reached the measuring limit of the current measuring unit 56.

Moreover, the judging unit 58 may judge the water W to be present between the pair of electrodes 52 within the reactant gas flow field in the case that the voltage within the application range applied to the pair of electrodes 52 and the electric current measured by the current measuring unit 56 are at least partially exponentially related, as indicated by the solid line L1 in FIG. 6. On the other hand, the judging unit 58 may judge short-circuiting to be occurring in the pair of electrodes 52 in the case that the voltage within the application range applied to the pair of electrodes 52 and the electric current measured by the current measuring unit 56 are not exponentially related, as indicated by the broken line L2 in FIG. 6.

In the case where, as described above, the first selected voltages and the second selected voltages are applied to the pair of electrodes 52 by the voltage applying unit 54, the judging unit 58 may compare a first ratio and a second ratio. The first ratio is a ratio at which the electric current flowing between the electrodes 52 changes when the first selected voltages are applied. The second ratio is a ratio at which the electric current flowing between the electrodes 52 changes when the second selected voltages are applied.

In the case of the water W being present between the pair of electrodes 52, the second ratio is larger than the first ratio.

Therefore, the judging unit 58 may judge the water W to be present between the pair of electrodes 52 in the case of the second ratio being larger than the first ratio.

On the other hand, when a proportional relationship holds between the applied voltage and the inter-electrodes 52 current, or when the inter-electrodes 52 current becomes constant at the measuring limit of the current measuring unit 56, the first ratio and the second ratio will have the same magnitude. Therefore, the judging unit 58 may judge short-circuiting to be occurring between the pair of electrodes 52 in the case of the second ratio not becoming larger than the first ratio.

The judging unit 58 may perform the above-described judgment of presence or absence of the water W under the following conditions. That is, the voltage applying unit 54 applies the detection voltage to the pair of electrodes 52 before applying the voltage changing within the application range to the electrodes. In the case that a detection current flowing between the pair of electrodes 52 has been detected by the current measuring unit 56 at a time of application of this detection voltage, the voltage applying unit 54 applies, to the pair of electrodes 52, the voltage changing within the application range, instead of the detection voltage. Then, based on the change in electric current measured by the current measuring unit 56, the judging unit 58 judges presence or absence of the water W within the reactant gas flow field.

The method of water detection according to the present embodiment will be described below with reference to FIG. 7, citing as an example the case where each of its steps are performed using the above-described water detecting device 10*a*. In the method of water detection, a detection voltage applying step (step S1 of FIG. 7) of applying the detection voltage to the pair of electrodes 52 is performed by the voltage applying unit 54. Next, the method proceeds to step S2, where it is judged whether the current measuring unit 56 is detecting the detection current or not, by the judging unit 58.

The judging unit 58, in the case where, in step S2, it has judged the detection current not to be being detected (step S2: NO), judges water W not to be present between the pair of electrodes 52 within the reactant gas flow field and short-circuiting between the electrodes 52 not to be occurring either. Then, processing of step S2 is repeated until the detection current is detected.

Figure 7:
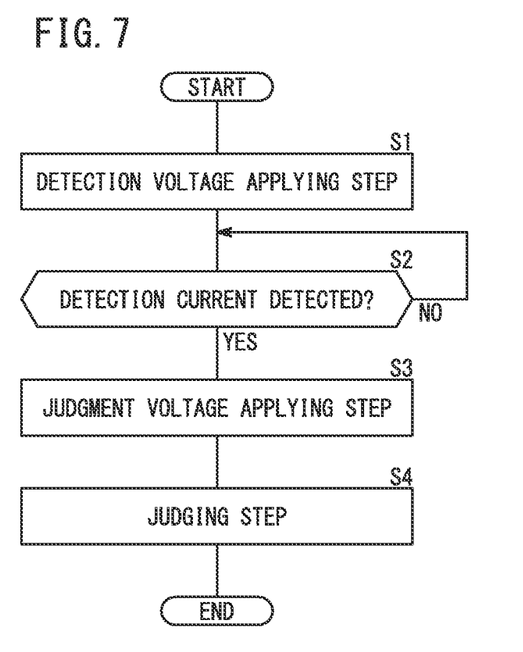
FIG. 7 is a flowchart describing a method of water detection according to the embodiment of the present invention.

The judging unit 58, in the case where, in step S2, it has judged the detection current to be being detected (step S2 in FIG. 7: YES), performs a judgment voltage applying step of step S3. In the judgment voltage applying step, the voltage applying unit 54 applies, to the pair of electrodes 52, the voltage changing within the application range.

Next, a judging step of step S4 is performed. In the judging step, presence or absence of water W within the reactant gas flow field is judged based on change in the electric current measured by the current measuring unit 56, as described above. After this processing of step S4, the flowchart according to the present embodiment ends.

As indicated above, in the water detecting devices 10*a*, 10*b* and method of water detection according to the present embodiment, presence or absence of water W is judged based on change in the electric current measured by the current measuring unit 56 when applying, to the pair of electrodes 52, the voltage changing within the application range. It is therefore possible to avoid a situation that short-circuiting of the electrodes 52, or the like, is mistakenly detected as water W being present between the electrodes 52. As a result, it becomes possible for detection accuracy of water W within the reactant gas flow field to be improved.

In the water detecting devices 10*a*, 10*b* according to the above-described embodiment, a configuration has been adopted in which the measuring limit of the current measuring unit 56 is set smaller than the current that flows between the pair of electrodes 52 when the first voltage and the second voltage are applied to the pair of electrodes 52 that are in short-circuit condition, and the judging unit 58 may judge water W to be present between the pair of electrodes 52 in the case that the second current measured by the current measuring unit 56 when the pair of electrodes 52 have been applied with the second voltage is larger than the first current measured by the current measuring unit 56 when the pair of electrodes 52 have been applied with the first voltage.

Moreover, in the method of water detection according to the above-described embodiment, a configuration has been adopted in which the measuring limit of the current measuring unit 56 is set smaller than the current that flows between the pair of electrodes 52 when the first voltage and the second voltage are applied to the pair of electrodes 52 that are in short-circuit condition, and in the judging step, water W may be judged to be present between the pair of electrodes 52 in the case that the second current measured by the current measuring unit 56 when the pair of electrodes 52 have been applied with the second voltage is larger than the first current measured by the current measuring unit 56 when the pair of electrodes 52 have been applied with the first voltage.

In these cases, it becomes possible for presence or absence of water W within the reactant gas flow field to be easily and efficiently judged by comparing the first current and the second current and confirming whether the second current is larger than the first current, or not.

In the water detecting devices 10*a*, 10*b* according to the above-described embodiment, a configuration has been adopted in which the judging unit 58 may judge water W to be present between the pair of electrodes 52 in the case that the voltage in the application range applied to the pair of electrodes 52 and the current measured by the current measuring unit 56 are at least partially exponentially related. Moreover, in the judging step of the method of water detection according to the above-described embodiment, a configuration has been adopted in which water W may be judged to be present between the pair of electrodes 52 in the case that the voltage in the application range applied to the pair of electrodes 52 and the current measured by the current measuring unit 56 are at least partially exponentially related.

In these cases, it becomes possible for presence or absence of water W within the reactant gas flow field to be highly accurately judged by confirming whether the voltage in the application range and the current measured by the current measuring unit 56 are at least partially exponentially related, or not. Note that the voltage in the application range and the current measured by the current measuring unit 56 may be wholly exponentially related.

In the water detecting devices 10*a*, 10*b* according to the above-described embodiment, a configuration has been adopted in which the voltage applying unit 54 is capable of applying the pair of electrodes 52 with a plurality of voltages selected from the first voltage range smaller than the electrolysis voltage of the water W (the first selected voltages), and of applying the pair of electrodes 52 with a plurality of voltages selected from the second voltage range larger than the electrolysis voltage of the water W (the second selected voltages), and the judging unit 58 may judge the water W to be present between the pair of electrodes 52 in the case that the first ratio with which the current flowing between the pair of electrodes 52 changes when the first selected voltages have been applied and the second ratio with which the current flowing between the pair of electrodes 52 changes when the second selected voltages have been applied, are compared, and the second ratio is larger than the first ratio.

Moreover, in the judgment voltage applying step of the method of water detection according to the above-described embodiment, a configuration may be adopted in which a plurality of voltages selected from the first voltage range smaller than the electrolysis voltage of the water W (the first selected voltages) are applied to the pair of electrodes 52, and a plurality of voltages selected from the second voltage range larger than the electrolysis voltage of the water W (the second selected voltages) are applied to the pair of electrodes 52, and in the judging step, the first ratio at which the current flowing between the pair of electrodes 52 changes when the first selected voltages are applied and the second ratio at which the current flowing between the pair of electrodes 52 changes when the second selected voltages are applied, are compared, and the water W is judged to be present between the pair of electrodes 52 in the case that the second ratio is larger than the first ratio.

In these cases, it becomes possible for presence or absence of water W within the reactant gas flow field to be easily and highly accurately judged by comparing the first ratio and the second ratio and confirming whether the second ratio is larger than the first ratio, or not.

In the water detecting devices 10*a*, 10*b* according to the above-described embodiment, a configuration has been adopted in which the voltage applying unit 54 is capable of applying the pair of electrodes 52 with the detection voltage which is larger than the electrolysis voltage of the water W, the current measuring unit 56 is capable of detecting the detection current that flows between the pair of electrodes 52 at the time of application of the detection voltage, and, in the case of the detection current having been detected by the current measuring unit 56, the voltage applying unit 54 changes the voltage applied to the pair of electrodes 52 in the application range, and the judging unit 58 judges presence or absence of the water W.

Moreover, in the method of water detection according to the above-described embodiment, a configuration may be adopted in which, prior to the judgment voltage applying step, there is included a detection voltage applying step of applying, to the pair of electrodes 52, the detection voltage which is larger than the electrolysis voltage of the water W, and the judgment voltage applying step and the judging step are performed in the case that the detection current flowing between the pair of electrodes 52 has been detected at the time of application of the detection voltage.

These cases result in that only in the case that there has been electrical conduction between the pair of electrodes 52 need judgment be made of whether the electrical conduction is due to water W interposing between the electrodes 52, or is due to short-circuiting between the electrodes 52. It therefore becomes possible for presence or absence of the water W within the reactant gas flow field to be easily and efficiently detected.

Note that in the water detecting devices 10*a*, 10*b* according to the present embodiment, application of the detection voltage by the voltage applying unit 54 is not an essential configuring element. Moreover, in the method of water detection according to the present embodiment, performing the detection voltage applying step prior to the judgment voltage applying step is not an essential configuring element.

The present invention is not limited to the above-mentioned embodiment, and may be variously modified in a range not departing from the spirit of the present invention.

Figure 8:
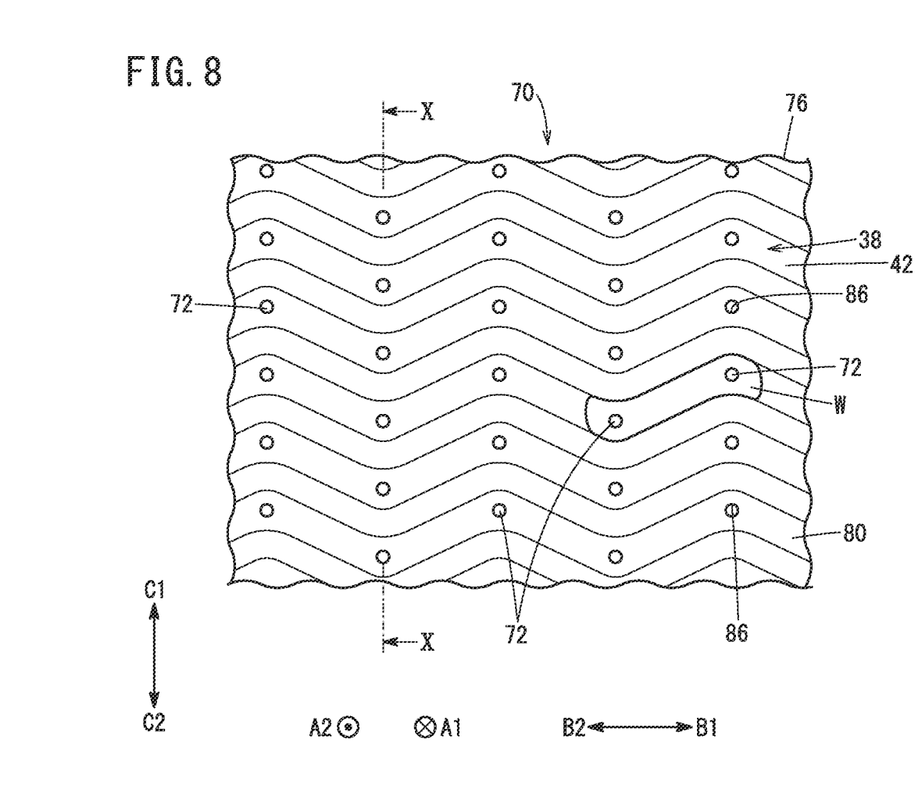
FIG. 8 is a diagram viewing from an oxygen-containing gas flow field side a second separator in which there have been incorporated electrodes of a water detecting device according to a modified example.
Figure 9:
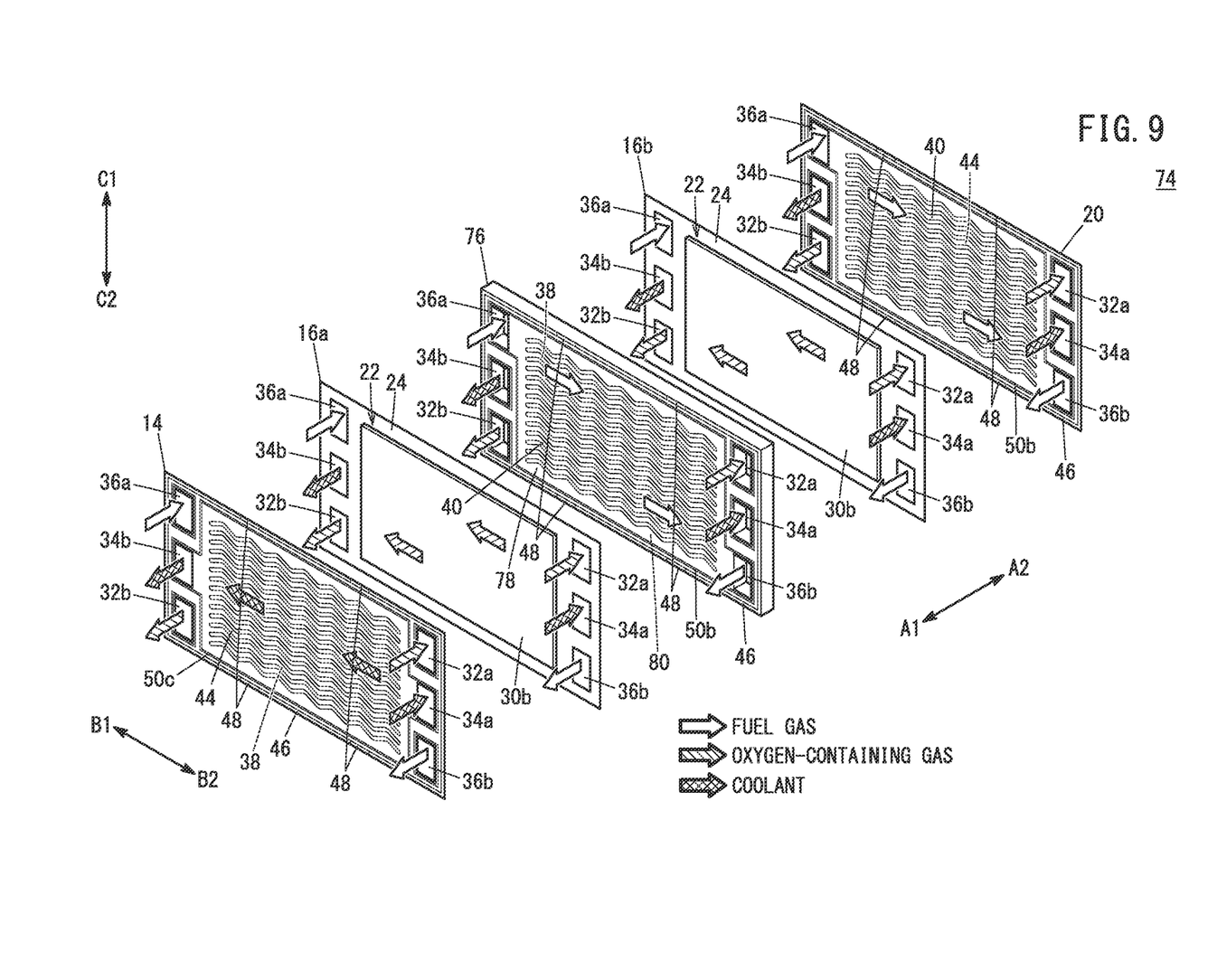
FIG. 9 is an exploded perspective view of a power generation cell including the second separator of FIG. 8.
Figure 10:
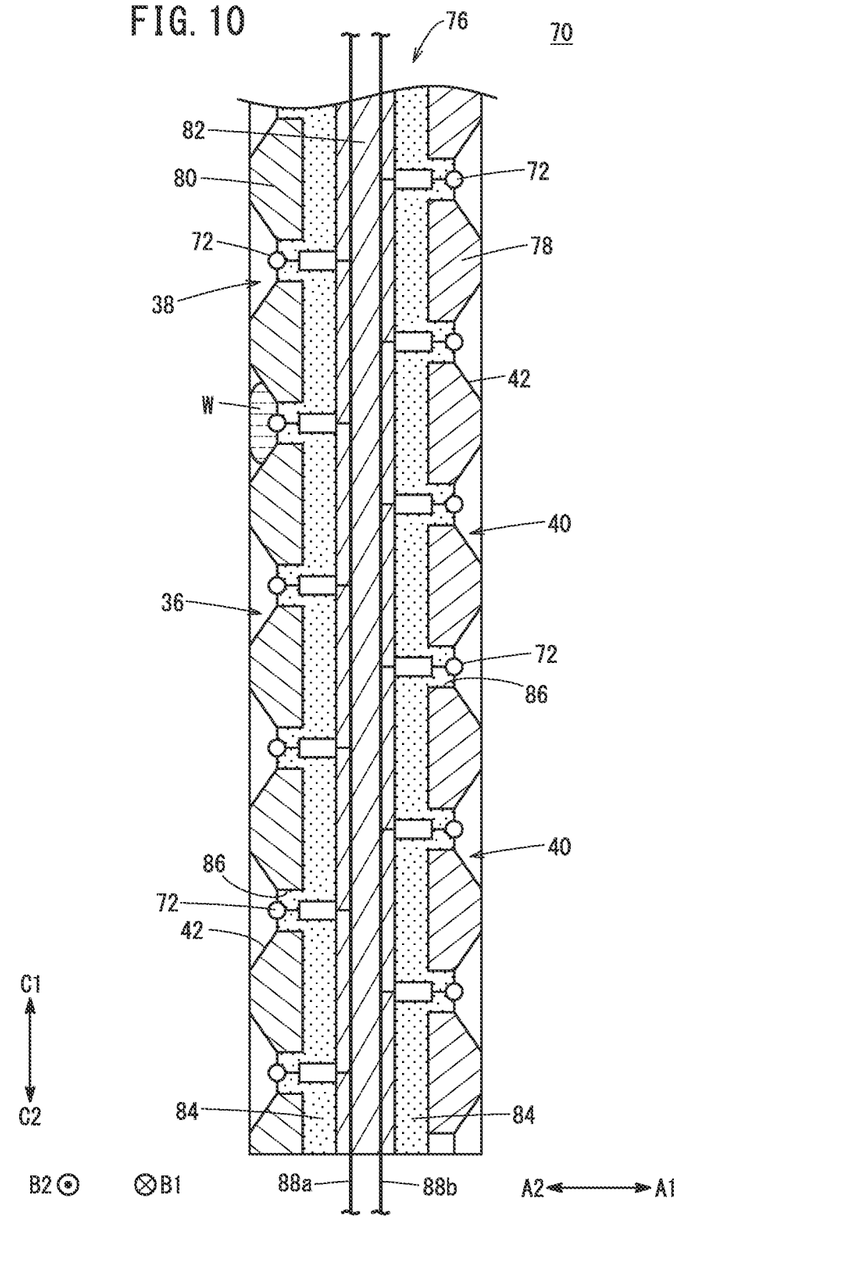
FIG. 10 is a cross-sectional view taken along the line X-X of the second separator of FIG. 8 looking in a direction of the arrows.

For example, electrodes 72 shown in FIGS. 8 and 10 may be provided instead of the electrodes 52 shown in FIGS. 1, 3, and 4, as in a water detecting device 70 according to a modified example of FIGS. 8 and 10. The electrodes 72 of FIGS. 8 and 10 are integrally incorporated in a second separator 76 of a power generation cell 74 shown in FIG. 9. Note that the second separator 76 of FIG. 9 may be employed to configure the power generation cell 74 instead of the second separator 18 of FIG. 2 only at a time of the likes of a performance test of the fuel cell stack. Moreover, the second separator 76 of FIG. 9 may be employed to configure the power generation cell 74 at a time of actual usage of the fuel cell stack.

As shown in FIG. 10, the second separator 76 has: an anode side plate 78; a cathode side plate 80; and a middle plate 82 sandwiched by these anode side plate 78 and cathode side plate 80. A space between the anode side plate 78 and the middle plate 82, and a space between the middle plate 82 and the cathode side plate 80 are each provided with a silver paste 84. Due to this silver paste 84, the anode side plate 78, the middle plate 82, and the cathode side plate 80 are integrally adhered. The anode side plate 78 and the cathode side plate 80 can be configured from the same material as the second separator 18 of FIG. 2. The middle plate 82 can be configured from a conductive material such as a metal.

A surface on the arrow A1 side of the anode side plate 78 is provided with the fuel gas flow field 40 similarly to the surface on the arrow A1 side of the second separator 18 of FIG. 2. A surface on the arrow A2 side of the cathode side plate 80 is provided with the oxygen-containing gas flow field 38 similarly to the surface on the arrow A2 side of the second separator 18 of FIG. 2.

As shown in FIGS. 8 and 10, a plurality of sets of pairs of electrodes 72 provided separated from each other, are provided at positions facing the fuel gas flow field 40 of the anode side plate 78. A plurality of sets of pairs of electrodes 72 provided separated from each other, are provided at positions facing the oxygen-containing gas flow field 38 of the cathode side plate 80. Each of the electrodes 72 faces the reactant gas flow field via a through-hole 86 that penetrates the anode side plate 78 and the cathode side plate 80 in a thickness direction (the arrows A1, A2 direction). Note that the number (number of sets), disposition, and so on, of these electrodes 72 are not specifically limited. Moreover, the electrodes 72 may be provided solely to either one of the fuel gas flow field 40 and the oxygen-containing gas flow field 38.

The middle plate 82 has arranged as wirings therein: a conductive member 88*a* which is connected to the electrodes 72 that face the oxygen-containing gas flow field 38; and a conductive member 88*b* which is connected to the electrodes 72 that face the fuel gas flow field 40. The voltage applying unit 54 and current measuring unit 56 of FIG. 1 provided outside the power generation cell 74 and the pairs of electrodes 72 are electrically connected via a conductive material. These conductive members 88*a*, 88*b* have wiring arrangements enabling each of the plurality of sets of electrodes 72 to be independently made electrically continuous. As a result, it becomes clear in which place of the fuel gas flow field 40 and the oxygen-containing gas flow field 38 the liquid water W is present.

In the water detecting device 70 comprising the electrodes 72 configured in the above-described way too, presence or absence of water W between the electrodes 72 within the reactant gas flow field can be detected similarly to in the water detecting devices 10a, 10b of FIG. 1, and operational advantages similar to those of the water detecting devices 10a, 10b of FIG. 1 can be obtained. That is, presence or absence of liquid water W is judged based on change in the electric current measured by the current measuring unit 56 when the voltage changing within the application range is applied to the pair of electrodes 72.

It is thus avoided that short-circuiting of the electrodes 72, or the like, is mistakenly detected as liquid water W being present between the electrodes 72. As a result, it becomes possible for detection accuracy of liquid water W within the reactant gas flow field to be improved.

What is claimed is:

1. A method of water detection for detecting presence or absence of liquid water within a reactant gas flow field through which a reactant gas flows along a membrane electrode assembly of a power generation cell, the method comprising:
    a voltage applying step of applying a voltage to a pair of electrodes provided at a position facing the reactant gas flow field, the electrodes being spaced from each other, the voltage changing within an application range that includes a first voltage and a second voltage, the first voltage being smaller than an electrolysis voltage of the water, the second voltage being larger than the electrolysis voltage of the water; and
    a judging step of judging presence or absence of water within the reactant gas flow field, based on change in electric current flowing between the pair of electrodes measured by a current measuring unit when the voltage changing within the application range is applied to the pair of electrodes,
    wherein:
    a measuring limit of the current measuring unit is set smaller than electric current that flows between the pair of electrodes when the voltage within the application range is applied to the pair of electrodes that are in short-circuit condition, and
    in the judging step, the water is judged to be present between the pair of electrodes in a case that a second current measured by the current measuring unit when the second voltage is applied to the pair of electrodes is larger than a first current measured by the current measuring unit when the first voltage is applied to the pair of electrodes.

2. The method of water detection according to claim 1, wherein
    in the judging step, the water is judged to be present between the pair of electrodes in a case that the voltage within the application range applied to the pair of electrodes and the electric current measured by the current measuring unit are at least partially exponentially related.

3. A method of water detection for detecting presence or absence of liquid water within a reactant gas flow field through which a reactant gas flows along a membrane electrode assembly of a power generation cell, the method comprising:
    a voltage applying step of applying a voltage to a pair of electrodes provided at a position facing the reactant gas flow field, the electrodes being spaced from each other, the voltage changing within an application range that includes a first voltage and a second voltage, the first voltage being smaller than an electrolysis voltage of the water, the second voltage being larger than the electrolysis voltage of the water; and
    a judging step of judging presence or absence of water within the reactant gas flow field, based on change in electric current flowing between the pair of electrodes measured by a current measuring unit when the voltage changing within the application range is applied to the pair of electrodes, wherein:
    in the judgment voltage applying step, a plurality of voltages selected from a first voltage range smaller than the electrolysis voltage of the water are applied to the pair of electrodes and a plurality of voltages selected from a second voltage range larger than the electrolysis voltage of the water are applied to the pair of electrodes, and
    in the judging step, a first ratio at which the electric current flowing between the pair of electrodes changes when the plurality of voltages selected from the first voltage range are applied, and a second ratio at which the electric current flowing between the pair of electrodes changes when the plurality of voltages selected from the second voltage range are applied, are compared, and the water is judged to be present between the pair of electrodes in a case that the second ratio is larger than the first ratio.

4. The method of water detection according to claim 1, further comprising:
    prior to the voltage applying step, a detection voltage applying step of applying, to the pair of electrodes, a detection voltage larger than the electrolysis voltage of the water.

* * * * *